(12) United States Patent
Maliverney et al.

(10) Patent No.: US 11,629,233 B2
(45) Date of Patent: Apr. 18, 2023

(54) FREE-RADICAL PHOTOINITIATORS AND USES OF SAME IN SILICONE COMPOSITIONS

(71) Applicants: Elkem Silicones France SAS, Lyons (FR); Universite de Haute Alsace, Mulhouse (FR)

(72) Inventors: Christian Maliverney, Saint Julien sur Bibost (FR); Perrine Theil, Saint Pierre de Chandieu (FR); Jean-Marc Frances, Meyzieu (FR); Xavier Allonas, Mulhouse (FR); Ahmad Ibrahim, Mulhouse (FR)

(73) Assignees: Elkem Silicones France SAS, Lyons (FR); Universite de Haute Alsace, Mulhouse (FR)

( * ) Notice: Subject to any disclaimer, the term of this patent is extended or adjusted under 35 U.S.C. 154(b) by 29 days.

(21) Appl. No.: 16/624,852

(22) PCT Filed: Jun. 21, 2018

(86) PCT No.: PCT/FR2018/000177
§ 371 (c)(1),
(2) Date: Dec. 19, 2019

(87) PCT Pub. No.: WO2018/234643
PCT Pub. Date: Dec. 27, 2018

(65) Prior Publication Data
US 2021/0332191 A1    Oct. 28, 2021

(30) Foreign Application Priority Data
Jun. 22, 2017   (FR) ..................... 1700671

(51) Int. Cl.
| | | |
|---|---|---|
| *C08L 83/06* | (2006.01) | |
| *C08G 77/14* | (2006.01) | |
| *B29C 64/295* | (2017.01) | |
| *B29C 64/277* | (2017.01) | |
| *B29C 64/10* | (2017.01) | |
| *B29C 35/08* | (2006.01) | |
| *C08J 3/28* | (2006.01) | |
| *C08K 5/00* | (2006.01) | |
| *C08F 2/46* | (2006.01) | |
| *C08L 83/04* | (2006.01) | |
| *C08F 4/00* | (2006.01) | |

(52) U.S. Cl.
CPC .......... *C08G 77/14* (2013.01); *B29C 35/0805* (2013.01); *B29C 64/10* (2017.08); *B29C 64/277* (2017.08); *B29C 64/295* (2017.08); *C08J 3/28* (2013.01); *C08K 5/0025* (2013.01); *C08L 83/06* (2013.01); *C08F 2/46* (2013.01); *C08F 4/00* (2013.01); *C08L 83/04* (2013.01)

(58) Field of Classification Search
CPC ............ C08F 83/04; C08F 83/06; C08F 4/00; C08F 2/46; C08L 83/04; C08L 83/06
See application file for complete search history.

(56) References Cited

U.S. PATENT DOCUMENTS

| | | | |
|---|---|---|---|
| 2,676,182 A | 4/1954 | Daudt et al. | |
| 3,159,601 A | 12/1964 | Ashby | |
| 3,159,602 A | 12/1964 | Hamilton et al. | |
| 3,220,972 A | 11/1965 | Lamoreaux | |
| 3,377,432 A | 4/1968 | Abbott et al. | |
| 3,419,593 A | 12/1968 | Willing | |
| 3,715,334 A | 2/1973 | Karstedt | |
| 3,814,730 A | 6/1974 | Karstedt | |
| 3,876,519 A * | 4/1975 | McGinniss ............... | C08K 5/45 522/26 |
| 4,101,558 A * | 7/1978 | Vacek .................. | C07D 335/16 522/53 |
| 4,585,669 A | 4/1986 | Eckberg | |

(Continued)

FOREIGN PATENT DOCUMENTS

| | | |
|---|---|---|
| CH | 666267 A5 | 7/1988 |
| CN | 103613989 A | 3/2014 |

(Continued)

OTHER PUBLICATIONS

English abstract JP 04-26687, Jan. 1992.*
PCT International Search Report for PCT/FR2018/000177, dated Sep. 17, 2018.
Miguel G. Neumann, et al., "The relation between the polymerization rates and swelling coefficients for copolymers obtained by photoinitiation," Polymer Testing, (2007), vol. 26,189-194.
J.O. Jilek, et al., "Neurotrope und psychotrope Substanzen VII. 2-Alkoxy-9-(3-dimethylaminopropyliden)thioxanthene and weitere Derivativen von Prothixen," Collection Czechoslov. Chem. Commun., (1966), vol. 31, 269-278.

(Continued)

*Primary Examiner* — Margaret G Moore
(74) *Attorney, Agent, or Firm* — McBee Moore & Vanik IP, LLC; Susan McBee; Thomas Visone (57) ABSTRACT

The present invention concerns type II photoinitiators for the free-radical crosslinking of silicone compositions, in particular acrylic silicone compositions. The present invention concerns a silicone composition C1 that can be crosslinked by exposure to radiation with a wavelength of between 300 and 450 nm, comprising: —at least one organopolysiloxane A comprising at least one methacrylate group bonded to a silicon atom, at least one organohydrogenopolysiloxane H comprising at least two, and preferably at least three hydrogen atoms each bonded to different silicon atoms, and—at least one free-radical photoinitiator P. The present invention also concerns the provision of a silicone composition that can be polymerized or crosslinked by free-radical process comprising a type II photoinitiator system suitable for crosslinking silicone compositions, in particular by exposure to radiation, and absorbing light radiation with a wavelength greater than 300 nm.

14 Claims, No Drawings

(56) References Cited

U.S. PATENT DOCUMENTS

| | | | |
|---|---|---|---|
| 4,661,595 A * | 4/1987 | Avar | C07C 45/46 |
| | | | 546/89 |
| 5,872,170 A * | 2/1999 | Mine | C08L 83/04 |
| | | | 524/440 |
| 6,451,870 B1 | 9/2002 | DeCato et al. | |
| 6,605,734 B2 | 8/2003 | Roy et al. | |
| 7,052,263 B2 | 5/2006 | John | |
| 2004/0170924 A1 | 9/2004 | Kunimoto et al. | |
| 2013/0190422 A1 * | 7/2013 | Kadobayashi | A61K 6/887 |
| | | | 523/115 |
| 2016/0001237 A1 | 1/2016 | Halbach | |
| 2017/0057980 A1 | 3/2017 | Boyer et al. | |
| 2019/0256654 A1 * | 8/2019 | Zhou | C08K 5/06 |

FOREIGN PATENT DOCUMENTS

| | | | |
|---|---|---|---|
| EP | 0057459 A1 | | 8/1982 |
| EP | 0070746 A1 | | 1/1983 |
| EP | 0188978 A1 | | 7/1986 |
| EP | 0190530 A1 | | 8/1986 |
| EP | 0281718 A2 | | 9/1988 |
| EP | 0940458 A1 | | 9/1999 |
| EP | 1235836 B1 | | 7/2004 |
| FR | 1528464 A | | 6/1968 |
| FR | 2372874 A1 | | 6/1978 |
| FR | 2632960 A1 | | 12/1989 |
| JP | S612031984 A | | 9/1986 |
| JP | S61203194 U | | 12/1986 |
| JP | 04-026687 | * | 1/1992 |
| JP | 09296113 A | | 11/1997 |
| JP | 2009203387 A | | 9/2009 |
| JP | 2016113392 A | | 6/2016 |
| KR | 20040007700 A | | 1/2004 |
| KR | 20150123278 A | | 11/2015 |
| RU | 2196784 C2 | | 1/2003 |
| WO | 2016044547 A1 | | 3/2016 |
| WO | 2016134972 A1 | | 9/2016 |
| WO | 2017007952 A1 | | 1/2017 |
| WO | 2017055747 A1 | | 4/2017 |

OTHER PUBLICATIONS

Gilles Michel Clavier, et al., "2,3-di-n-alkoxyanthraquinones as gelators of organic solvents,"J Chem. Soc., Perkin Trans. 2, (1998), 2527-2534.

Yi Hu, et al., "Side Chain position, length and odd/even effects on the 2D-self assembly of mono-substituted anthraquinone derivatives at the liquid/solid interface," The Royal Society of Chemistry, (2015), vol. 5, 93337-93346.

Jefferson, A., et al., "Gas—liquid chromatography of naturally occurring xanthones and related derivatives," Journal of Chromatography A., (1971) vol. 57, 247-254.

* cited by examiner

FREE-RADICAL PHOTOINITIATORS AND USES OF SAME IN SILICONE COMPOSITIONS

CROSS-REFERENCE TO RELATED APPLICATIONS

This application is the National Stage entry of International Application No. PCT/FR2018/000177, filed 21 Jun. 2018, which claims priority to French Patent Application No. 1700671, filed 22 Jun. 2017.

BACKGROUND

Field

The present invention relates to type II photoinitiators for free-radical crosslinking of silicone compositions, notably of acrylic silicone compositions.

Description of Related Art

The use of plastic films as substrate materials for coating silicone coatings in order to create release coatings requires appropriate technology. In fact, most of these plastic films are heat-sensitive. Thus, dimensional deformation of the film occurs during coating and drying of the silicone layer in heating ovens under the combined effect of the tensile forces and of the temperature to which the films are subjected. The technology for crosslinking functional silicone oils under ultraviolet (UV) radiation makes it unnecessary to use high temperatures, so that the release layers can be crosslinked without affecting the substrates. Moreover, this technology offers the advantage of attaining high productivity without being energy-consuming, and without using solvents. Plastic substrates are materials of choice for numerous applications and their use is steadily increasing. Thus, research and innovation efforts are indispensable in the field of the crosslinking of thin films of silicone under UV.

Silicone compositions are generally crosslinked under UV or visible radiation emitted by doped or undoped mercury vapor lamps whose emission spectrum extends from 200 nm to the visible (>400 nm). Light sources such as light-emitting diodes, better known by the acronym LEDs, which deliver point-source UV or visible light may also be used.

Generally speaking, crosslinking under irradiation is promoted by a photoinitiator molecule. Photoinitiators and uses thereof are discussed extensively in the literature. In the field of free-radical polymerization of acrylic silicone compositions, the photoinitiator molecules commonly used are the so-called type I photoinitiators. Under irradiation, these molecules decompose and produce free radicals. These radicals induce the polymerization initiating reaction, which leads to hardening of the compositions. Much effort has been expended in developing type I photoinitiators possessing characteristics allowing them to be used in acrylic silicone formulations to obtain release coatings. Throughout the application, the expression "type I photoinitiators" means compounds that are well known by a person skilled in the art, and are able to generate polymerization-initiating free radicals under UV excitation by intramolecular homolytic fragmentation.

There are also type II photoinitiator systems comprising a free-radical photoinitiator and a co-initiator. In type II photoinitiator systems, the photoinitiators used are capable of generating polymerization-initiating free radicals by reaction with another compound called a co-initiator, said reaction causing transfer of a hydrogen from the co-initiator to said photoinitiator. The photoinitiators used in the type II photoinitiator systems are denoted by the expression "type II photoinitiators".

To date, no type II photoinitiator system exists, comprising a free-radical photoinitiator and a co-initiator, effective for polymerization of acrylic silicone compositions under UV or visible radiation emitted by light sources such as light-emitting diodes, better known by the acronym LEDs, which generate a light beam with a narrow output spectrum centered on a specific wavelength. LEDs with UV or visible radiation mainly have an emission band centered on a wavelength of 365, 385, 395 or 405 nm.

SUMMARY

The aim of the present invention is to supply a free-radical polymerizable or crosslinkable silicone composition comprising a type II photoinitiator system suitable for crosslinking silicone compositions, notably by exposure to UV or visible radiation emitted by light-emitting diodes. LED lamps offer advantages in terms of electric power consumption, service life and electrical safety compared to the lamps with mercury or xenon sources commonly used until now. Another advantage of LEDs is absence of a warm-up time, which gives gains in productivity.

Another aim of the present invention is to supply a free-radical polymerizable or crosslinkable silicone composition comprising a type II photoinitiator system suitable for crosslinking silicone compositions, notably by exposure to radiation, and which absorbs light of wavelength above 300 nm.

Another aim of the present invention is to supply a method for preparing a film or a coating on a substrate starting from the free-radical polymerizable silicone composition according to the invention.

Another aim of the present invention is to supply a substrate coated with a film or a coating obtained from the free-radical polymerizable silicone composition according to the invention.

Another aim of the present invention is to supply silicone compositions for obtaining release coatings that crosslink under radiation, and notably under UV radiation, starting from polyorganosiloxanes comprising (meth)acrylate groups, notably (meth)acrylic ester groups or else epoxy acrylates or polyether acrylates.

Another aim of the present invention is to supply a silicone composition that is free-radical polymerizable or crosslinkable by exposure to radiation and by polyaddition. These silicone compositions with a dual crosslinking system have the particular feature of being able to crosslink partially very quickly by irradiation and then continue crosslinking by heating, to obtain a silicone elastomer with good stability and good mechanical properties.

Silicone compositions with a dual crosslinking system are described in U.S. Pat. No. 4,585,669 (GE). Silicone compositions comprising an organohydrogenopolysiloxane, a polyorganosiloxane comprising acrylate radicals, a polyorganosiloxane comprising vinyl groups, a Pt catalyst and a photoinitiator of the free-radical type are described. The combination of diethoxyacetophenone as photoinitiator and benzophenone as photosensitizer is illustrated.

Silicone compositions with a dual crosslinking system ("dual cure silicone compositions") are definitely of interest for use in 3D printing as they make it possible to increase the printing speed of silicone elastomer items. Irradiation of the layers of silicone compositions as printing proceeds allows rapid gelation of a part of the composition during production and thus each layer retains its shape without collapse of the printed structure.

When printing is finished, a heating step makes it possible to end crosslinking of the composition by polyaddition to obtain a silicone elastomer with good stability and good mechanical properties.

Patent application WO2016/134972 describes a method of producing a silicone elastomer article with an extrusion or inkjet 3D printer. This patent application employs a silicone composition that is crosslinked both by UV irradiation and by heating. The irradiation leads to gelation of the layers and the final thermal hardening leads to a silicone elastomer with good stability and mechanical properties. The only photoinitiator described is an Irgacure® 651 commercial type I photoinitiator, which corresponds to 2,2-dimethoxy-2-phenylacetophenone. UV radiation of wavelength 360 nm is used in the examples.

Patent application WO2017/07952 also describes silicone compositions for additive manufacturing comprising a first reagent polymerizable by irradiation and a second system of reagents crosslinkable among other things by polyaddition. In this patent application, additive manufacturing is carried out either in a tank by continuous liquid interface production (CLIP) or by inkjet. A combination of morpholinone and isopropylthioxanthone is described as the photoinitiator. The poor solubility of the photoinitiator is illustrated in the examples. A centrifugation step is necessary for separating any undissolved photoinitiator. Moreover, owing to the presence of an amino group, morpholinone is an inhibitor of the polyaddition reaction. Generally photoinitiators absorbing at wavelengths between 200 and 500 nm are described.

Consequently, there is a need to develop silicone compositions that are crosslinkable by irradiation under UV or visible radiation of wavelength above 300 nm emitted by light-emitting diodes and by polyaddition using a photoinitiator that is soluble in the silicone composition.

Another aim of the present invention is to supply a silicone composition that is free-radical polymerizable or crosslinkable by exposure to radiation and by polyaddition and is useful for the methods of additive manufacturing also known as 3D printing processes.

Thus, the present invention relates to a silicone composition C1 crosslinkable by exposure to radiation with a wavelength between 300 and 450 nm, comprising:
at least one polyorganosiloxane A comprising at least one (meth)acrylate group bound to a silicon atom,
at least one organohydrogenopolysiloxane H comprising at least two, and preferably at least three hydrogen atoms each bound to different silicon atoms, and
at least one free-radical photoinitiator P of the following formula (I):

(I)

in which:
the symbol X is selected from the group consisting of: an oxygen atom, a sulfur atom, a $CH_2$ group and a carbonyl radical,
the symbols $R^2$ and $R^4$ are hydrogen atoms,
the symbols $R^1$ and $R^3$, which may be identical or different, are selected from the group consisting of: a hydrogen atom, a hydroxyl and a group of formula —OZ with the symbol O being an oxygen atom and the symbol Z being selected from the group consisting of:
a $C_1$-$C_{20}$, preferably $C_3$-$C_{20}$, alkyl group or $C_2$-$C_{20}$ alkenyl group,
a group —(C=O)—$R^5$, the radical $R^5$ being selected from the $C_1$-$C_{20}$ alkyl, $C_2$-$C_{20}$ alkenyl, $C_3$-$C_{20}$ cycloalkyl and $C_6$-$C_{12}$ aryl groups, and
a group —Si($R^6$)$_3$, where the groups $R^6$, which may be identical or different, are selected from the $C_1$-$C_{20}$ alkyl, $C_2$-$C_{20}$ alkenyl, $C_3$-$C_{20}$ cycloalkyl, $C_6$-$C_{12}$ aryl, $C_1$-$C_{20}$ alkoxyl groups and the hydrogen atom,
and with the condition that at least one of the substituents $R^1$ or $R^3$ is a hydroxyl or a group of formula —OZ.

DETAILED DESCRIPTION OF A PREFERRED EMBODIMENT

For the purpose of obtaining photocrosslinking under radiation, the composition comprises a type II photoinitiator system which, under the effect of absorption of the incident light energy, releases free radicals in the medium. These radicals perform the role of initiators of free-radical polymerization of the (meth)acrylic functions. Since it is the vector of hardening of the composition, the photoinitiator system is an essential key of this application.

The present invention is therefore based on the use of a specific type II photoinitiator system comprising the combination of a free-radical photoinitiator P as defined above and an organohydrogenopolysiloxane H as co-initiator.

The silicone composition C1 has the advantage of crosslinking efficiently by exposure to UV or visible radiation. Moreover, the free-radical photoinitiator P of formula (I) has the advantage of being more soluble in polyorganosiloxanes comprising at least one (meth)acrylate group than the commercial free-radical photoinitiators such as benzophenone or isopropylthioxanthone.

Throughout the present document, we shall refer to elements of conventional nomenclature to denote the siloxy units M, D, T, Q of the polyorganosiloxanes, which according to the designations widely known in silicone chemistry represent:
M=siloxy unit of formula $R_3SiO_{1/2}$
D=siloxy unit of formula $R_2SiO_{2/2}$
T=siloxy unit of formula $RSiO_{3/2}$ and
Q=siloxy unit of formula $SiO_{4/2}$,
where the radicals R, which may be identical or different, are monovalent groups.

All the viscosities discussed in the present account correspond to a magnitude of dynamic viscosity at 25° C. (unless stated otherwise) called "Newtonian", i.e. dynamic viscosity that is measured, in a manner known per se, with a Brookfield viscosimeter at a shear rate gradient low enough for the viscosity measured to be independent of the shear rate gradient.

The crosslinkable silicone compositions C1 according to the invention comprise at least one polyorganosiloxane A comprising at least one (meth)acrylate group bound to a silicon atom. As representative examples of (meth)acrylate functions borne by the silicone and quite particularly suitable for the invention, we may more particularly mention the acrylate and methacrylate derivatives, ethers of (meth)acrylates and esters of (meth)acrylates bound to the polysiloxane chain by an Si—C bond.

According to one embodiment, the polyorganosiloxane A comprises:

a1) at least one unit of the following formula (A1):

$$R_aZ_bSiO_{(4-a-b)/2} \quad (A1)$$

in which:
the symbols R, which may be identical or different, each represent a linear or branched $C_1$ to $C_{18}$ alkyl group, a $C_6$ to $C_{12}$ aryl or aralkyl group, optionally substituted, preferably with halogen atoms, or an alkoxy radical —$OR^4$ with $R^4$ being a hydrogen atom or a hydrocarbon radical comprising from 1 to 10 carbon atoms,
the symbols Z are monovalent radicals of formula -y-(Y')$_n$ in which:
y represents a linear or branched polyvalent $C_1$-$C_{18}$ alkylene radical optionally extended by $C_1$ to $C_4$ divalent oxyalkylene or polyoxyalkylene radicals optionally substituted with a hydroxy radical,
Y' represents a monovalent alkenylcarbonyloxy radical, and
n is equal to 1, 2 or 3, and
"a" is an integer equal to 0, 1 or 2, b is an integer equal to 1 or 2 and the sum a+b=1, 2 or 3; and a2) optionally units of the following formula (A2):

$$R_aSiO_{(4-a)/2} \quad (A2)$$

in which:
the symbols R, which may be identical or different, each represent a linear or branched $C_1$ to $C_{18}$ alkyl group, a $C_6$ to $C_{12}$ aryl or aralkyl group, optionally substituted, preferably with halogen atoms, and
"a" is an integer equal to 0, 1, 2 or 3.

In the above formulas (A1) and (A2), the symbol R may advantageously represent a monovalent radical selected from the group consisting of: methyl, ethyl, propyl, 3,3,3-trifluoropropyl, xylyl, tolyl and phenyl.

The polyorganosiloxane A may have a linear, branched, cyclic or network structure. When they are linear polyorganosiloxanes, the latter may consist essentially of:
siloxy units "D" selected from the units of formulas $R_2SiO_{2/2}$, $RZSiO_{2/2}$ and $Z_2SiO_{2/2}$;
siloxy units "M" selected from the units of formulas $R_3SiO_{1/2}$, $R_2ZSiO_{1/2}$, $RZ_2SiO_{1/2}$ and $Z_3SiO_{1/2}$, and
the symbols R and Z are as defined above in formula (A1).

According to one embodiment, in the above formula (A1), among the aforementioned alkenylcarbonyloxy radicals Y', we may mention the acryloxy radical [$CH_2$=CH—CO—O—] and the methacryloxy radicals: [($CH_3$)CH=CH—CO—O—] and [$CH_2$=C($CH_3$)—CO—O—].

As an illustration of the symbol y for said symbol Z in the units of formula (A1), we may mention the radicals:
—$CH_2$—;
—$(CH_2)_2$—;
—$(CH_2)_3$—;
—$CH_2$—CH($CH_3$)—$CH_2$—;
—$(CH_2)_3$—NH—$CH_2$—$CH_2$—;
—$(CH_2)_3$—$OCH_2$—;
—$(CH_2)_3$—[O—$CH_2$—CH($CH_3$)—]—;
—$(CH_2)_3$—O—$CH_2$—CH(OH)(—$CH_2$—);
—$(CH_2)_3$—O—$CH_2$—C($CH_2$—$CH_3$)[—$(CH_2)_2$—]$_2$;
and
—$(CH_2)_2$—$C_6H_9$(OH)—.

Preferably, the polyorganosiloxane A corresponds to the following formula (III):

$$R^3-\underset{\underset{R^1}{|}}{\overset{\overset{R^1}{|}}{Si}}-O\left[-\underset{\underset{R^1}{|}}{\overset{\overset{R^1}{|}}{Si}}-O\right]_a\left[-\underset{\underset{\underset{\underset{\underset{R^1-Si-R^1}{|}}{O}}{[R^1-Si-R^2]_c}}{O}}{\overset{\overset{R^1}{|}}{Si}}-O\right]\left[-\underset{\underset{R^2}{|}}{\overset{\overset{R^1}{|}}{Si}}-O\right]_b-\underset{\underset{R^1}{|}}{\overset{\overset{R^1}{|}}{Si}}-R^3 \quad (III)$$

in which:
the symbols $R^1$, which may be identical or different, each represent a linear or branched $C_1$ to $C_{18}$ alkyl group, a $C_6$ to $C_{12}$ aryl or aralkyl group, optionally substituted, preferably with halogen atoms, or an alkoxy radical —$OR^4$ with $R^4$ being a hydrogen atom or a hydrocarbon radical comprising from 1 to 10 carbon atoms,
the symbols $R^2$ and $R^3$, which may be identical or different, each represent either a radical $R^1$ or a monovalent radical of formula Z=-w-(Y')$_n$ in which:
w represents a linear or branched polyvalent $C_1$-$C_{18}$ alkylene radical optionally extended by divalent $C_1$ to $C_4$ oxyalkylene or polyoxyalkylene radicals optionally substituted with a hydroxy radical,
Y' represents a monovalent alkenylcarbonyloxy radical, and
n is equal to 1, 2 or 3, and
with a=0 to 1000, b=0 to 500, c=0 to 500, d=0 to 500 and a+b+c+d=0 to 2500, and
with the condition that at least one symbol $R^2$ or $R^3$ represents the monovalent radical of formula Z.

According to a preferred embodiment, in the above formula (III):
c=0, d=0, a=1 to 1000, b=1 to 250, the symbol $R^2$ represents the monovalent radical of formula Z and the symbols $R^1$ and $R^3$ have the same meaning as above.

Even more preferably, in the above formula (III):
c=0, d=0, a=1 to 500, b=1 to 100, the symbol $R^2$ represents the monovalent radical of formula Z and the symbols $R^1$ and $R^3$ have the same meaning as above.

According to one embodiment, the polyorganosiloxane A according to the invention corresponds to the following formula (IV):

$$-\underset{|}{\overset{|}{Si}}-O-(\underset{|}{\overset{|}{Si}}-O)_x-(\underset{|}{\overset{|}{Si}}-O)_n-\underset{|}{\overset{|}{Si}}- \quad (IV)$$

[structure with pendant group: —$CH_2CH_2CH_2$—O—$CH_2$—CH(OH)—$CH_2$—O—C(=O)—CH=$CH_2$]

in which:

x is between 1 and 1000;

n is between 1 and 100.

The organohydrogenopolysiloxane H comprises at least two, and preferably at least three hydrogen atoms each bound to different silicon atoms.

The expression "a hydrogen atom bound to a silicon atom" means a function Si—H or a bond Si—H or a hydrogen-silyl function.

According to a preferred embodiment, the organohydrogenopolysiloxane H comprises:

(i) at least two units of formula (H1), in which:

L represents a monovalent radical different from a hydrogen atom,

H represents the hydrogen atom, d and e represent integers, d having a value of 1 or 2, e a value of 0, 1 or 2 and (d+e) a value of 1, 2 or 3;

(ii) and optionally other units of formula (H2):

in which:

L has the same meaning as above, and f represents an integer with a value of 0, 1, 2 or 3.

In the above formulas (H1) and (H2), it is understood that if several groups L are present, they may be identical to or different from one another. In formula (H1), the symbol d may preferably have a value of 1. Moreover, in formula (H1) and in formula (H2), L may preferably represent a monovalent radical selected from the group consisting of an alkyl group having 1 to 8 carbon atoms, optionally substituted with at least one halogen atom, and an aryl group. L may advantageously represent a monovalent radical selected from the group consisting of methyl, ethyl, propyl, 3,3,3-trifluoropropyl, xylyl, tolyl and phenyl.

Examples of units of formula (H1) are as follows: $H(CH_3)_2SiO_{1/2}$, $H(CH_3)SiO_{2/2}$ and $H(C_6H_5)SiO_{2/2}$.

The organohydrogenopolysiloxane H may have a linear, branched, cyclic or network structure. When they are linear organohydrogenopolysiloxanes, the latter may consist essentially of:

siloxy units "D" selected from the units of formulas $HLSiO_{2/2}$ (also called unit D') and $L_2SiO_{2/2}$; and siloxy units "M" selected from the units of formulas $HL_2SiO_{1/2}$ (also called unit M') and $L_3SiO_{2/2}$, with the symbol L having the same meaning as above and the symbol H denoting a hydrogen atom.

These linear organohydrogenopolysiloxanes H may be oils having a dynamic viscosity at 25° C. between 1 mPa·s and 100 000 mPa·s, preferably between 1 mPa·s and 5000 mPa·s, and even more preferably between 1 mPa·s and 2000 mPa·s.

When they are cyclic organohydrogenopolysiloxanes, they may consist of siloxy units "D" selected from the units of formulas $HLSiO_{2/2}$ and $L_2SiO_{2/2}$, or of siloxy units of formula $HLSiO_{2/2}$ only. The units of formula $L_2SiO_{2/2}$ may notably be dialkylsiloxy units or alkarylsiloxy units. These cyclic organohydrogenopolysiloxanes may have a dynamic viscosity at 25° C. between 1 mPa·s and 5000 mPa·s.

Examples of organohydrogenopolysiloxane H are:

polydimethylsiloxanes with hydrogenodimethylsilyl ends;

poly(dimethylsiloxane-co-hydrogenomethylsiloxane)s with trimethylsilyl ends;

poly(dimethylsiloxane-co-hydrogenomethylsiloxane)s with hydrogenodimethylsilyl ends;

polyhydrogenomethylsiloxanes with trimethylsilyl ends; and cyclic hydrogenomethylpolysiloxanes.

When they are branched or network organohydrogenopolysiloxanes H, they may further comprise:

siloxy units "T" selected from the units of formulas $HSiO_{3/2}$ and $LSiO_{3/2}$;

siloxy units "Q" of formula $SiO_{4/2}$, with the symbol H representing a hydrogen atom and L having the same meaning as above.

According to one embodiment, the organohydrogenopolysiloxane H comprises at least 0.05 mol of Si—H functions per 100 g of polymer, preferably at least 0.08 mol of Si—H functions per 100 g of polymer, more preferably between 0.08 mol and 2.5 mol of Si—H functions per 100 g of polymer, and even more preferably between 0.08 mol and 1.8 mol of Si—H functions per 100 g of polymer.

The silicone composition C1 comprises a free-radical photoinitiator P of the following formula (I):

in which:

the symbol X is selected from the group consisting of: an oxygen atom, a sulfur atom, a $CH_2$ group and a carbonyl radical, the symbols $R^2$ and $R^4$ are hydrogen atoms, the symbols $R^1$ and $R^3$, which may be identical or different, are selected from the group consisting of: a hydrogen atom, a hydroxyl and a group of formula —OZ with the symbol O being an oxygen atom and the symbol Z being selected from the group consisting of:

a $C_1$-$C_{20}$, preferably $C_3$-$C_{20}$, alkyl group or $C_2$-$C_{20}$ alkenyl group, a group —(C=O)—$R^5$, with the radical $R^5$ being selected from the $C_1$-$C_{20}$ alkyl, $C_2$-$C_{20}$ alkenyl, $C_3$-$C_{20}$ cycloalkyl and $C_6$-$C_{12}$ aryl groups, and a group —Si($R^6$)$_3$, where the groups $R^6$, which may be identical or different, are selected from the $C_1$-$C_{20}$ alkyl, $C_2$-$C_{20}$ alkenyl, $C_3$-$C_{20}$ cycloalkyl, $C_6$-$C_{12}$ aryl, $C_1$-$C_{20}$ alkoxyl groups and the hydrogen atom, and with the condition that at least one of the substituents $R^1$ or $R^3$ is a hydroxyl or a group of formula —OZ.

According to an advantageous embodiment of the invention, in the above formula (I), $R^2=R^3=R^4=H$ and $R^1=OH$ or —OZ as defined above.

According to another embodiment, in the above formula (I), $R^1=R^2=R^4=H$ and $R^3=OH$ or —OZ as defined above.

According to one embodiment, the free-radical photoinitiator P is selected from the group consisting of the thioxanthone derivatives of the following formula (Ia):

(Ia)

in which:
the symbol X is a sulfur atom,
the symbols $R^2$ and $R^4$ are hydrogen atoms,
the symbols $R^1$ and $R^3$, which may be identical or different, are selected from the group consisting of: a hydrogen atom, a hydroxyl and a group of formula —OZ with the symbol O being an oxygen atom and the symbol Z being selected from the group consisting of:
a $C_1$-$C_{20}$, preferably $C_3$-$C_{20}$, alkyl group or $C_2$-$C_{20}$ alkenyl group,
a group —(C=O)—$R^5$, with the radical $R^5$ being selected from the $C_1$-$C_{20}$ alkyl, $C_2$-$C_{20}$ alkenyl, $C_3$-$C_{20}$ cycloalkyl and $C_6$-$C_{12}$ aryl groups, and
a group —Si($R^6$)$_3$, where the groups $R^6$, which may be identical or different, are selected from the $C_1$-$C_{20}$ alkyl, $C_2$-$C_{20}$ alkenyl, $C_3$-$C_{20}$ cycloalkyl, $C_6$-$C_{12}$ aryl, $C_1$-$C_{20}$ alkoxyl groups and the hydrogen atom,
and with the condition that at least one of the substituents $R^1$ or $R^3$ is a hydroxyl or a group of formula —OZ.

According to an advantageous embodiment of the invention, in formula (Ia) above, $R^2$=$R^3$=$R^4$=H and $R^1$=OH or —OZ as defined above.

According to another embodiment, in formula (Ia) above, $R^1$=$R^2$=$R^4$=H and $R^3$=OH or —OZ as defined above.

As examples of free-radical photoinitiators P of formula (Ia) we may notably mention the following compounds:
2-hydroxy-9H-thioxanthen-9-one, RN-CAS=31696-67-0,
2-methoxy-9H-thioxanthen-9-one, RN-CAS=40478-82-8,
2-ethoxy-9H-thioxanthen-9-one, RN-CAS=5543-66-8,
2-hexyloxy-9H-thioxanthen-9-one, RN-CAS=5596-56-5,
2-octyloxy-9H-thioxanthen-9-one, formula (6) hereunder
2-decyloxy-9H-thioxanthen-9-one, formula (7) hereunder
2-dodecyloxy-9H-thioxanthen-9-one, formula (8) hereunder
2-acetyloxy-9H-thioxanthen-9-one, RN-CAS=92439-12-8,
2-[(trimethylsilyl)oxy]-9H-thioxanthen-9-one, formula (17) hereunder
2-propenoic acid 9-oxo-9H-thioxanthen-2-yl ester RN-CAS=113797-58-3,
2-neodecanoic acid 9-oxo-9H-thioxanthen-2-yl ester, formula (20) hereunder
4-neodecanoic acid 9-oxo-9H-thioxanthen-2-yl ester, formula (25) hereunder and
4-hydroxy-9H-thioxanthen-9-one, formula (23) hereunder.

According to another embodiment, the free-radical photoinitiator P is selected from the group consisting of the xanthone derivatives, of the following formula (Ib):

(Ib)

in which:
the symbol X is an oxygen atom,
the symbols $R^2$ and $R^4$ are hydrogen atoms,
the symbols $R^1$ and $R^3$, which may be identical or different, are selected from the group consisting of: a hydrogen atom, a hydroxyl and a group of formula —OZ with the symbol O being an oxygen atom and the symbol Z being selected from the group consisting of:
a $C_1$-$C_{20}$, preferably $C_3$-$C_{20}$, alkyl group or $C_2$-$C_{20}$ alkenyl group,
a group —(C=O)—$R^5$, with the radical $R^5$ being selected from the $C_1$-$C_{20}$ alkyl, $C_2$-$C_{20}$ alkenyl, $C_3$-$C_{20}$ cycloalkyl and $C_6$-$C_{12}$ aryl groups, and
a group —Si($R^6$)$_3$, where the groups $R^6$, which may be identical or different, are selected from the $C_1$-$C_{20}$ alkyl, $C_2$-$C_{20}$ alkenyl, $C_3$-$C_{20}$ cycloalkyl, $C_6$-$C_{12}$ aryl, $C_1$-$C_{20}$ alkoxyl groups and the hydrogen atom,
and with the condition that at least one of the substituents $R^1$ or $R^3$ is a hydroxyl or a group of formula —OZ.

According to an advantageous embodiment of the invention, in the above formula (Ib), $R^2$=$R^3$=$R^4$=H and $R^1$=OH or —OZ as defined above.

According to another embodiment, in the above formula (Ib), $R^1$=$R^2$=$R^4$=H and $R^3$=OH or —OZ as defined above.

As examples of free-radical photoinitiators P of formula (Ib), we may notably mention the following compounds:
2-hydroxy-9H-xanthen-9-one, RN-CAS=1915-98-6,
2-methoxy-9H-xanthen-9-one, RN-CAS=1214-20-6,
2-ethoxy-9H-xanthen-9-one, RN-CAS=103573-60-0,
2-hexyloxy-9H-xanthen-9-one, formula (1) hereunder
2-octyloxy-9H-xanthen-9-one, formula (2) hereunder
2-decyloxy-9H-xanthen-9-one, formula (3) hereunder
2-dodecyloxy-9H-xanthen-9-one, formula (4) hereunder
2-[(trimethylsilyl)oxy]-9H-xanthen-9-one, RN-CAS=32747-67-4, formula (18) hereunder,
2-neodecanoic acid 9-oxo-9H-xanthen-2-yl ester, formula (19) hereunder
4-neodecanoic acid 9-oxo-9H-xanthen-2-yl ester, formula (24) hereunder and
4-hydroxy-9H-xanthen-9-one RN-CAS=14686-63-6.

According to one embodiment, the free-radical photoinitiator P is selected from the group consisting of the anthracenone derivatives, of the following formula (Ic):

(Ic)

in which:
the symbol X is a $CH_2$ group,
the symbols $R^2$ and $R^4$ are hydrogen atoms,
the symbols $R^1$ and $R^3$, which may be identical or different, are selected from the group consisting of: a hydrogen atom, a hydroxyl and a group of formula —OZ with the symbol O being an oxygen atom and the symbol Z being selected from the group consisting of:
a $C_1$-$C_{20}$, preferably $C_3$-$C_{20}$, alkyl group or $C_2$-$C_{20}$ alkenyl group, a group —(C=O)—$R^5$, with the radical $R^5$ being selected from the $C_1$-$C_{20}$ alkyl, $C_2$-$C_{20}$ alkenyl, $C_3$-$C_{20}$ cycloalkyl and $C_6$-$C_{12}$ aryl groups, and a group —Si($R^6$)$_3$, where the groups $R^6$, which may be identical or different, are selected from the $C_1$-$C_{20}$ alkyl, $C_2$-$C_{20}$ alkenyl, $C_3$-$C_{20}$ cycloalkyl, $C_6$-$C_{12}$ aryl, $C_1$-$C_{20}$ alkoxyl groups and the hydrogen atom, and with the condition that at least one of the substituents $R^1$ or $R^3$ is a hydroxyl or a group of formula —OZ.

According to an advantageous embodiment of the invention, in the above formula (Ic), $R^2$=$R^3$=$R^4$=H and $R^1$=OH or —OZ as defined above.

According to another embodiment, in the above formula (Ic), $R^1$=$R^2$=$R^4$=H and $R^3$=OH or —OZ as defined above.

As examples of free-radical photoinitiators P derived from of anthracenone of formula (Ic), we may mention 2-methoxy-10H-anthracen-9-one (RN-CAS=53604-95-8) and 4-methoxy-10H-anthracen-9-one (RN CAS=7470-93-1) as well as the compounds of formula (13), (14), (15), (16) and (22) hereunder.

According to one embodiment, the free-radical photoinitiator P is selected from the group consisting of the derivatives of anthraquinone, of the following formula (Id):

in which:
the symbol X is a carbonyl radical,
the symbols $R^2$ and $R^4$ are hydrogen atoms,
the symbols $R^1$ and $R^3$, which may be identical or different, are selected from the group consisting of: a hydrogen atom, a hydroxyl and a group of formula —OZ with the symbol O being an oxygen atom and the symbol Z being selected from the group consisting of:
a $C_1$-$C_{20}$, preferably $C_3$-$C_{20}$, alkyl group or $C_2$-$C_{20}$ alkenyl group,
a group —(C=O)—$R^5$, with the radical $R^5$ being selected from the $C_1$-$C_{20}$ alkyl, $C_2$-$C_{20}$ alkenyl, $C_3$-$C_{20}$ cycloalkyl and $C_6$-$C_{12}$ aryl groups, and
a group —Si($R^6$)$_3$, where the groups $R^6$, which may be identical or different, are selected from the $C_1$-$C_{20}$ alkyl, $C_2$-$C_{20}$ alkenyl, $C_3$-$C_{20}$ cycloalkyl, $C_6$-$C_{12}$ aryl, $C_1$-$C_{20}$ alkoxyl groups and the hydrogen atom,
and with the condition that at least one of the substituents $R^1$ or $R^3$ is a hydroxyl or a group of formula —OZ.

According to an advantageous embodiment of the invention, in the above formula (Id), $R^2$=$R^3$=$R^4$=H and $R^1$=OH or —OZ as defined above.

According to another embodiment, in the above formula (Id), $R^1$=$R^2$=$R^4$=H and $R^3$=OH or —OZ as defined above.

As examples of free-radical photoinitiators P derived from anthraquinone of formula (Id), we may mention 2-dodecyloxy-10H-anthraquin-9-one (RN-CAS=218961-85-4) and octanoic acid, 9,10-dihydro-9,10-dioxo-2-anthracenyl ester (RN-CAS=110484-84) as well as the compounds of formula (9), (10), (11), (12) and (21) hereunder.

According to an advantageous embodiment, the free-radical photoinitiator P is selected from the derivatives of thioxanthone of formula (Ia) and of xanthone of formula (Ib) as described above. The derivatives of xanthones absorbing at 365 nm and the derivatives of thioxanthones absorbing at 395 nm are preferred as they can be used with LEDs.

According to one embodiment, the crosslinkable silicone compositions C1 according to the invention comprise at least 0.0003 mol of free-radical photoinitiator P per 100 g of composition C1, and preferably at least 0.0005 mol of free-radical photoinitiator P per 100 g of composition C1. Preferably, the content in moles of free-radical photoinitiator P in the compositions C1 of the invention is between 0.0003 and 0.015 mol per 100 g of composition C1, and even more preferably between 0.0005 and 0.015 mol per 100 g of composition C1.

According to one embodiment, the composition C1 does not comprise platinum.

The crosslinkable silicone compositions C1 according to the invention may further comprise at least one additive. As additive, we may include at least one additive controlling the force of detachment of a silicone/adhesive interface in the composition that is selected from:
(i) (meth)acrylate organic derivatives, and
(ii) silicones with (meth)acrylate function(s).

The epoxidized (meth)acrylate compounds, (meth)acryloglyceropolyesters, (meth)acrylo-urethanes, (meth)acrylopolyethers, (meth)acrylopolyesters, and (meth)acrylo-acrylic compounds are notably suitable as (meth)acrylate organic derivatives. Trimethylolpropane triacrylate, tripropylene glycol diacrylate and pentaerythritol tetraacrylate are more particularly preferred.

According to a preferred variant of the invention, the additive used is a silicone with (meth)acrylate function(s). As a representative of (meth)acrylate functions borne by the silicone and quite particularly suitable for the invention, we may more particularly mention the acrylate and methacrylate derivatives, ethers of (meth)acrylates and esters of meth(acrylates) bound to the polysiloxane chain by an Si—C bond. Acrylate derivatives of this kind are notably described in patents EP 0 281 718, FR 2 632 960 and EP 0 940 458.

The present invention also relates to the use of the composition C1 according to the invention for preparing silicone films with release properties.

Preferably, for preparing these silicone films, compositions C1 as defined above are used in which the ratio of the number of moles of photoinitiator P to the number of moles of Si—H functions in the organohydrogenopolysiloxane B is between 0.5 and 20, preferably between 1 and 5, said organohydrogenopolysiloxane B preferably comprising at least 0.08 mol, preferably between 0.1 mol and 2.5 mol, of Si—H functions per 100 g.

The present invention also relates to a silicone elastomer obtained by crosslinking a composition C1 as defined above.

The present invention also relates to a method for preparing silicone films with release properties, comprising a step of crosslinking a composition C1 as defined above.

Preferably, in the method for preparing silicone films with release properties according to the invention, compositions C1 as defined above are used in which the ratio of the number of moles of free-radical photoinitiator P to the number of moles of Si—H functions in the organohydrogenopolysiloxane B is between 0.5 and 20, preferably between 1 and 5, said organohydrogenopolysiloxane B preferably comprising at least 0.08 mol, preferably between 0.1 mol and 2.5 mol, of Si—H functions per 100 g of organohydrogenopolysiloxane B.

According to one embodiment of the method of the invention, the crosslinking step is carried out under air or under inert atmosphere. Preferably, this crosslinking step is carried out under inert atmosphere.

According to one embodiment, the crosslinking step of the method according to the invention is carried out with radiation with a wavelength between 200 nm and 450 nm, preferably under inert atmosphere.

According to a preferred embodiment, the crosslinking step of the method according to the invention is carried out with radiation with a wavelength between 300 nm and 450 nm, preferably under inert atmosphere.

The present invention also relates to a method for preparing a coating on a substrate, comprising the following steps:
applying a crosslinkable composition C1 as defined above on a substrate, and
crosslinking said composition C1 by exposure to radiation with a wavelength between 200 nm and 450 nm.

The radiation may be emitted by doped or undoped mercury vapor lamps whose emission spectrum extends from 200 nm to the visible. Light sources such as light-emitting diodes, better known by the acronym LEDs, which deliver point source UV or visible light, may also be used.

According to a preferred embodiment of the method according to the invention, the radiation is generated by light-emitting diodes and even more preferably the radiation is generated by light-emitting diodes with an emission band centered on a wavelength of 365, 385, 395 or 405 nm.

The irradiation time may be short and it is generally less than 1 minute, preferably less than 10 seconds and may be of the order of some hundredths of a second for small coating thicknesses. The crosslinking obtained is excellent even in the absence of any heating.

According to one embodiment, the crosslinking step is carried out at a temperature between 10° C. and 50° C., preferably between 15° C. and 35° C.

Of course, the hardening rate may be controlled, notably by the number of lamps used, by the duration of exposure to the radiation and by the distance between the composition and the lamp or lamps.

The composition C1 according to the invention without solvent, i.e. undiluted, may be applied using devices capable of depositing small amounts of liquid uniformly. For this purpose it is possible to use for example the device called "Helio glissant" comprising in particular two superposed rolls: the role of the bottom roll, which dips into the coating tank containing the compositions, is to impregnate the upper roll with a very thin layer, its role then being to deposit, on the paper, the desired amounts of the compositions with which it is impregnated, this metering being obtained by controlling the respective speed of the two counterrotating rolls.

The amounts of composition C1 deposited on the substrates are variable and are most often between 0.1 and 5 g/m² of treated surface. These amounts depend on the nature of the substrates and the release properties required. Most often they are between 0.5 and 1.5 g/m² for nonporous substrates.

This method is particularly suitable for preparing a silicone release coating on a substrate which is a flexible substrate of textile, paper, polyvinyl chloride, polyester, polypropylene, polyamide, polyethylene, polyethylene terephthalate, polyurethane or nonwoven glass fibers.

These coatings are particularly suitable for use in the anti-adherence field.

The present invention therefore also relates to a coated substrate obtainable by the method as defined above. As noted above, the substrate may be a flexible substrate of textile, paper, polyvinyl chloride, polyester, polypropylene, polyamide, polyethylene, polyethylene terephthalate, polyurethane or nonwoven glass fibers.

The coated substrates have an antiadherent, water-repellent character, or give improved surface properties such as slipperiness, stain resistance or softness.

Another aspect of the invention relates to a silicone composition C2 crosslinkable thermally and by exposure to radiation with a wavelength between 300 and 450 nm comprising:
at least one composition C1 as described above,
at least one polyorganosiloxane B comprising at least two alkenyl units bound to silicon atoms and
at least one hydrosilylation catalyst.

In this composition C2, the organohydrogenopolysiloxane H performs the role of free-radical co-initiator and crosslinking agent for the hydrosilylation reaction.

Throughout this patent application, "crosslinking" means hardening of the composition by reactions of polymerization of the meth(acrylate) functions, by reactions of polyaddition between the Si—H bonds of the organohydrogenopolysiloxanes H and the alkenyl groups of the polyorganosiloxanes B or by a combination of the two.

The term "thermally crosslinkable silicone composition" denotes a silicone composition capable of hardening by heating at a temperature generally between 60 and 220° C., preferably between 80 and 180° C.

The term "silicone composition crosslinkable by exposure to radiation" denotes a silicone composition capable of hardening by exposure to radiation.

According to one embodiment of the invention, the polyorganosiloxane B comprises:
(i) at least two siloxy units (I.5) of the following formula $$W_a Z_b SiO_{\frac{4-(a+b)}{2}} \quad (1.5)$$

in which:
a=1 or 2, b=0, 1 or 2 and a+b=1, 2 or 3;
W represents independently an alkenyl group, preferably having from 2 to 6 carbon atoms, and even more preferably a vinyl or allyl group, and
Z represents independently a monovalent hydrocarbon-containing group having from 1 to 30 carbon atoms and preferably selected from the group consisting of the alkyl groups having from 1 to 8 carbon atoms inclusive, and even more preferably selected from the group consisting of a methyl, ethyl, propyl and 3,3,3-trifluoropropyl radical,
(ii) and optionally other siloxy units (I.6) of the following formula $$Z_c SiO_{(4-c)/2} \quad (I.6)$$

in which:
Z has the same meaning as above, and
c represents an integer with a value of 0, 1, 2 or 3.

The polyorganosiloxane B may have a linear structure, optionally cyclic. These linear polyorganosiloxanes have a dynamic viscosity at 25° C. between 100 mPa·s and 1000000 mPa·s and more preferably between 1000 mPa·s and 120000 mPa·s.

When the polyorganosiloxane B has a linear formula, in formula (I.5), a=1 and a+b=2 or 3 and in formula (I.6) c=2 or 3. It is understood that in the above formulas (I.5) and (I.6) if several radicals W and Z are present, they may be identical to or different from one another.

In the case of linear polyorganosiloxanes, they may be selected from the group consisting of:
- polydimethylsiloxanes with dimethylvinylsilyl ends;
- poly(vinylmethylsiloxane-co-dimethylsiloxane)s with dimethylvinylsilyl ends;
- poly(dimethylsiloxane-co-vinylmethylsiloxane)s with trimethylsilyl ends and
- cyclic polymethylvinylsiloxanes.

The polyorganosiloxane B may have a branched structure. It is then called silicone resin. Advantageously they are silicone resins comprising from 0.1 to 20 wt %, preferably from 4 to 20 wt %, of $C_2$-$C_6$ alkenyl groups bound to silicon atoms. The alkenyl groups may be located on M, D or T siloxy units. These resins may be prepared for example by the method described in U.S. Pat. No. 2,676,182, 0.1 to 20%. Preferably the alkenyl groups are selected from vinyls, allyls and hexenyls.

In a preferred embodiment of the invention, the silicone resin comprises at least two vinyl radicals and is selected from the group consisting of the following silicone resins:
- $MD^{Vi}Q$ where the vinyl groups are included in D units,
- $MD^{Vi}TQ$ where the vinyl groups are included in D units,
- $MM^{Vi}Q$ where the vinyl groups are included in a proportion of the M units,
- $MM^{Vi}TQ$ where the vinyl groups are included in a proportion of the M units,
- $MM^{Vi}DD^{Vi}Q$ where the vinyl groups are included in a proportion of the M and D units, and mixtures thereof,
with:
- $M^{Vi}$=siloxy unit of formula $(R)_2(vinyl)SiO_{1/2}$
- $D^{Vi}$=siloxy unit of formula $(R)(vinyl)SiO_{2/2}$ and the groups R, which may be identical or different, are monovalent hydrocarbon-containing groups selected from the alkyl groups having from 1 to 8 carbon atoms inclusive such as the methyl, ethyl, propyl and 3,3,3-trifluoropropyl groups and the aryl groups such as xylyl, tolyl and phenyl. Preferably, the groups R are methyls.

Preferably the silicone resin has the formula $MD^{Vi}Q$ or $MM^{Vi}Q$ as described above.

The polyaddition catalysts K are well known. Compounds of platinum and of rhodium are preferably used. We may, in particular, use the complexes of platinum and of an organic product described in U.S. Pat. Nos. 3,159,601, 3,159,602, 3,220,972 and the European patents EP-A-0 057 459, EP-A-0 188 978 and EP-A-0 190 530, the complexes of platinum and of vinylated organosiloxanes described in U.S. Pat. Nos. 3,419,593, 3,715,334, 3,377,432 and 3,814,730, the complexes of platinum with carbene ligands as described in EP1235836, the platinum-diene complexes as described in U.S. Pat. No. 6,605,734 and US20170057980. The photoactivatable hydrosilylation catalysts as described in WO2016044547 may also be used. Other polyaddition catalysts based on complexes of base metals such as iron, nickel and cobalt may also be used. According to a preferred embodiment of the invention, the catalyst K is based on platinum. In this case, the amount by weight of catalyst K, calculated as weight of platinum metal, is generally between 2 and 400 ppm, preferably between 5 and 200 ppm based on the total weight of the composition C2.

Advantageously, the content of platinum metal in the composition C2 is between 10 and 120 ppmw, preferably between 10 and 95 ppmw, more preferably between 10 and 70 ppmw and even more preferably between 10 and 60 ppmw based on the total weight of the composition C2.

The silicone compositions C2 may moreover contain at least one of the following compounds:
- an inhibitor I,
- fillers F and
- adhesion promoters G.

As filler F, we may use reinforcing mineral fillers or semi-reinforcing or filling mineral fillers. The reinforcing mineral fillers may be selected from siliceous materials. The siliceous reinforcing fillers are selected from colloidal silicas, powders of fumed silica and of precipitated silica or a mixture thereof. These powders have an average particle size generally below 0.1 μm and a BET specific surface area above 50 m$^2$/g, preferably between 150 and 350 m$^2$/g. These silicas may be incorporated as they are or after being treated with organosilicon compounds usually employed for this application. These compounds include methylpolysiloxanes such as hexamethyldisiloxane, octamethylcyclotetrasiloxane, methylpolysilazanes such as hexamethyldisilazane, hexamethylcyclotrisilazane, chlorosilanes such as dimethyldichlorosilane, trimethylchlorosilane, methylvinyldichlorosilane, dimethylvinylchlorosilane, alkoxysilanes such as dimethyldimethoxysilane, dimethylvinylethoxysilane, trimethylmethoxysilane. Siliceous semi-reinforcing fillers such as diatomaceous earths or ground quartz may also be used.

Semireinforcing or filling mineral fillers may be added in addition to or instead of the reinforcing silicas. Examples of these nonsiliceous fillers, usable alone or mixed, are calcium carbonate, optionally surface-treated with an organic acid or with an ester of an organic acid, baked clay, titanium dioxide of the rutile type, the oxides of iron, zinc, chromium, zirconium, or magnesium, the various forms of alumina (whether or not hydrated), boron nitride, lithopone, barium metaborate, barium sulfate and glass microspheres. These fillers are coarser, generally with an average particle diameter greater than 0.1 μm and a specific surface area generally less than 30 m$^2$/g. These fillers may have been surface-modified by treatment with the various organosilicon compounds usually employed for this application.

Conductive fillers such as nano-objects based on graphene or carbon nanotubes may also be used.

According to one embodiment of the invention, a reinforcing filler F is used, which is a fumed silica having a specific surface area measured by the BET method between 100 and 400 m$^2$/g. Even more advantageously, the reinforcing filler F is a fumed silica having a specific surface area measured by the BET method between 100 and 400 m$^2$/g and which has been treated with organosilicon compounds.

According to a particular embodiment of the invention, the silicone composition C2 comprises from 1 to 40 parts by weight of filler F, preferably from 1 to 25 parts by weight of filler F and more preferably from 1 to 15 parts of filler F per 100 parts by weight of silicone composition C2.

The crosslinking inhibitor I (or retarder of the polyaddition reaction) may for its part be selected from the following compounds:
- a polyorganosiloxane, advantageously cyclic, and substituted with at least one alkenyl, tetramethylvinyltetrasiloxane being particularly preferred,
- phosphines and organic phosphites,
- unsaturated amides,
- alkylated maleates
- and acetylenic alcohols.

These acetylenic alcohols (cf. FR-B-1 528 464 and FR-A-2 372 874), which form part of the preferred thermal blockers of the hydrosilylation reaction, have the formula (I1):

$(R^1)(R^2)C(OH)-C\equiv CH$ (I1)

in which:
- $R^1$ is a linear or branched alkyl radical, or a phenyl radical;
- $R^2$ is a hydrogen atom, a linear or branched alkyl radical, or a phenyl radical;
- the radicals $R^1$, $R^2$ and the carbon atom at the alpha position of the triple bond that may optionally form a ring; and
- the total number of carbon atoms contained in $R^1$ and $R^2$ being at least 5, preferably from 9 to 20.

Said alcohols are preferably selected from those having a boiling point above 250° C. As examples, we may mention the following commercially available products:
ethynyl-1-cyclohexanol-1;
methyl-3-dodecyn-1-ol-3;
trimethyl-3,7,11-dodecyn-1-ol-3;
diphenyl-1,1-propyn-2-ol-1;
ethyl-3-ethyl-6-nonyn-1-ol-3;
methyl-3-pentadecyn-1-ol-3.

A crosslinking inhibitor I of this kind is present at a rate of 3000 ppm at most, preferably at a rate of 100 to 2000 ppm relative to the total weight of the composition C2.

As adhesion promoters G, it will be possible to use the adhesion promoters usually employed in this field. For example, it will be possible to use:
- a silane or vinylated polyorganosiloxane alone or partially hydrolyzed as well as a reaction product thereof,
- a silane or polyorganosiloxane functionalized with an epoxy function alone or partially hydrolyzed as well as a reaction product thereof,
- a polyorganosiloxane comprising at least one SiH function and at least one function selected from the group consisting of: epoxy functions, (meth)acrylate functions, alkoxy functions and vinyl functions,
- a metal alkoxide or a chelate of a metal such as Ti, Zr, Al, for example tert-butyl titanate.

The invention also relates to a silicone elastomer obtained by crosslinking a composition C2 as defined above.

These silicone elastomers may be used in multiple applications, for example such as in the medical field in "woundcare": the care and treatment of wounds or injuries (coating of dressings, manufacture of external prostheses, cushions for preventing pressure sores), or for encapsulation of electronic components or as coatings, notably for coating flexible paper or plastic films as well as for coating textiles, notably vehicle airbags.

Another aspect of the invention relates to a method for preparing articles made of silicone elastomer, comprising a step of crosslinking a composition C2 as defined above by exposure to radiation with a wavelength between 300 nm and 450 nm.

Advantageously, in the above method, the radiation is generated by light-emitting diodes and even more advantageously the radiation is generated by light-emitting diodes with an emission band centered on a wavelength of 365, 385, 395 or 405 nm.

The method for preparing articles made of silicone elastomer according to the invention may further comprise a step of heating, preferably at a temperature between 60 and 220° C., even more preferably between 80 and 180° C.

The present invention also relates to the use of the composition C2 according to the invention for preparing articles made of silicone elastomer by methods of additive manufacturing, also known as 3D printing processes.

This description generally comprises the designation ASTM F2792-12a, "Standard terminology for additive manufacturing technologies". According to this ASTM standard, a "3D printer" is defined as "a machine used for 3D printing" and "3D printing" is defined as "the manufacture of objects by depositing a material by means of a printing head, a nozzle or some other printer technology".

Additive manufacturing "AM" is defined as a process for joining materials for manufacturing objects based on data of a 3D model, generally layer by layer, as opposed to the methods of subtractive manufacture. The synonyms associated with 3D printing and covered by 3D printing comprise additive manufacturing, additive processes, additive techniques and layer-by-layer manufacture. Additive manufacturing (AM) may also be called rapid prototyping (RP). As used here, "3D printing" is interchangeable with "additive manufacturing".

In general, all the 3D printing processes have a common starting point, which is a computer-generated data source or a program that can describe an object. The computer-generated data source or program may be based on a real or a virtual object. For example, a real object may be scanned using a 3D scanner and the digitization data may be used for creating the computer-generated data source or program. Alternatively, the computer-generated data source or program may be designed from scratch. The computer-generated data source or program is generally converted to a standard language (STL) file format. However, other file formats may be used. The file is generally read in the 3D printing software, which takes the file and optionally the user input for separating it into "slices", the number of which may reach several thousand. The 3D printing software generally delivers the machine instructions, which may be in the form of G-code, which is read by the 3D printer to construct each slice. The machine instructions are transferred to the 3D printer, which then constructs the object, layer by layer, as a function of this data sequence in the form of machine instructions. The thicknesses of these layers may vary.

The silicone compositions C2 according to the invention make it possible to increase the printing speed of silicone elastomer items. Irradiation of the layers of silicone compositions as printing proceeds allows rapid gelation of a part of the composition during production and thus each layer retains its shape without collapse of the printed structure. When printing is finished, a heating step makes it possible to finish the crosslinking of the composition by polyaddition to obtain a silicone elastomer with good stability and good mechanical properties.

Advantageously, the silicone compositions C2 according to the invention may be used for the 3D printing processes using tank photopolymerization, extrusion of material or deposition of material by adapting the viscosity of the silicone composition C2 to the technology used.

Tank photopolymerization is an additive manufacturing process according to which a hardenable liquid resin contained in a tank is selectively hardened when polymerization of its molecular chains is triggered by ultraviolet light. Tank photopolymerization may use a lamp or light-emitting diodes (LEDs) as the UV energy source. When used in additive manufacturing processes such as tank photopolymerization, the viscosity of the silicone composition C2 will be between 10 mPa·s and 100000 mPa·s, preferably between 100 and 10000 mPa·s and even more preferably between 100 and 2000 mPa·s.

A "3D tank" printer is a printer as described in application WO2017/055747, where a device for UV-visible illumination comprises a light source based on LEDs and a mask adapted for transmitting or blocking irradiation according to a display pattern for creating a projection image. The mask thus comprises a matrix of pixels configured to assume an on-state allowing irradiation and an off-state blocking irradiation. The on-state is reflected in transmission of radiation toward the corresponding point of the projection image. The blocking state is reflected in absence of transmission of the radiation toward the corresponding point of the projection image. The display pattern corresponds to the distribution of the states of said pixels.

The manufacturing system of the tank printer therefore comprises a system for irradiation preferably with UV-visible LEDs, a mask adapted for cutting off the UV-visible radiation emitted by the LEDs according to a display pattern for creating a projection image emitted by the irradiation device. The printer comprises a system for moving the projection image over a working surface, which is arranged in a container called a tank. The tank contains the silicone formulation having a working surface exposed to the projection image emitted by the irradiation device.

The tank manufacturing system may correspond to a working surface and irradiation of a layer of silicone formulation with the open side from above but also another possible configuration is irradiation from below through a bottom that is transparent to the radiation. In this case the working surface is the surface in contact with the transparent bottom. Adhesion of the working surface directly in contact with the transparent bottom is avoided by creating an inhibition layer in contact with the transparent bottom by oxygenation of the surface of the transparent bottom. An example of printer and of process according to a projection mode from below is described in U.S. Pat. No. 7,052,263.

Extrusion of materials is an additive manufacturing process in which a filament of material is extruded and distributed selectively through a nozzle. The flow rate of extruded material can be controlled by among other things the pressure exerted on the nozzle or the temperature.

Deposition of material is an additive manufacturing process in which fine droplets of a material are deposited selectively by printheads similar to those of paper printers. This process is also known as inkjet.

For use in additive manufacturing processes such as extrusion or deposition of material, the viscosity of the silicone composition C2 will be between 100 mPa·s and 1000000 mPa·s, preferably between 1000 mPa·s and 300000 mPa·s and even more preferably between 3000 and 200000 mPa·s. For this use, the silicone composition C2 must display thixotropic behavior (decrease of viscosity during shearing and increase of viscosity after shearing).

A "3D extrusion" printer is a 3D printer where the material is extruded through a nozzle, a syringe or an orifice during the additive manufacturing process. The extrusion of material generally functions by extruding the material through a nozzle, a syringe or an orifice for printing a cross section of an object, which may be repeated for each subsequent layer. The material extruded bonds to the layer located thereunder during hardening of the material. In a preferred embodiment, the process for printing a three-dimensional silicone elastomer article uses an extrusion 3D printer. The silicone compositions are extruded through a nozzle. The nozzle may be heated to facilitate distribution of the silicone composition for addition crosslinking. The average diameter of the nozzle defines the thickness of the layer. In one embodiment, the diameter of the layer is between 50 and 2000 µm, preferably between 100 and 800 µm and most preferably between 100 and 500 µm. The distance between the nozzle and the substrate is an important parameter for ensuring a good shape. It must be between + to/−30% of the average nozzle diameter. The dual cure silicone composition for radical crosslinking and polyaddition to be distributed through the nozzle may be supplied from a system of the cartridge type. The cartridge may comprise a nozzle or nozzles with an associated fluid reservoir or fluid reservoirs. It is also possible to use a coaxial system of two cartridges with a static mixer and a single nozzle. The pressure will be adapted to the fluid to be distributed, to the associated average nozzle diameter and to the printing speed.

Owing to the high shearing rate that occurs during extrusion from the nozzle, the viscosity of the silicone compositions is reduced considerably and thus allows printing of thin layers. The cartridge pressure may vary from 1 to 20 bar, preferably between 2 and 10 bar and most preferably between 4 and 7 bar. When nozzle diameters under 100 µm are used, the cartridge pressure must be above 20 bar to obtain good extrusion of the material. Suitable equipment using aluminum cartridges must be used in order to withstand such a pressure. The nozzles platform and/or platform moves in the X-Y plane (horizontal plane) to complete the cross section of the object, before moving in the plane of the Z axis (vertical) once a layer is completed. The nozzle has a high precision of XYZ movement. Once each layer is printed in the working plane X, Y, the nozzle is displaced in the Z direction only sufficiently for the next layer to be applied in the working location X, Y. In this way, the object that becomes the 3D article is constructed one layer at a time from bottom to top.

As described above, the distance between the nozzle and the preceding layer is an important parameter for ensuring good shape. It must be between + to/−30% of the average nozzle diameter. The printing speed is between 1 and 50 mm/s, preferably between 5 and 30 mm/s in order to obtain the best compromise between good precision and speed of manufacture.

A "3D inkjet" printer is defined as additive manufacturing equipment in which droplets of silicone formulation are deposited selectively. The silicone formulation is applied by means of a printing head in the form of individual droplets, discontinuously, at the desired location of the working plane (jetting). This is 3D equipment and a process for step by step production of 3D structures with an arrangement of printing head comprising at least one, preferably 2 to 200 printhead nozzles, allowing selective application of a formulation, or if applicable a plurality of formulations. The application of silicones by inkjet printing imposes specific requirements on the viscosity of the materials. In a printer for 3D spraying of the silicone formulation, one or more reservoirs are subjected to a pressure and are connected by a measuring line to a metering nozzle. Upstream or downstream of the reservoir, there may be devices that make it possible to homogenize and/or evacuate the dissolved gases so that the silicone compositions are homogeneous. One or more spray units operating independently of one another may be present, in order to construct the elastomer article starting from different silicone compositions for crosslinking by addition or, in the case of more complex structures, to give composite parts made of silicone elastomers and other plastics. Owing to the high shearing rate that occurs in the metering valve in the jetting procedure, the viscosity of these silicone com- positions for crosslinking by addition is lowered considerably and thus gives a jet of very fine microdroplets. Once the microdroplet has been deposited on the substrate, there is a sudden reduction of its shear rate, so that its viscosity increases again. As a result, the deposited drop quickly reaches a very high viscosity and thus allows precise construction of three-dimensional structures. The individual metering nozzles can be positioned accurately in the x, y and z directions to allow accurate deposition of targeted droplets of silicone on the substrate or, in the subsequent formation of shaped parts, on the addition of a crosslinkable silicone composition. It is desirable to use a UV and/or visible irradiation system for initiating hardening after printing each layer to avoid collapse of the structure.

Typically, the 3D printer uses one or more distributors, e.g. a nozzle or a printhead, for printing the hardenable silicone composition. Optionally, the distributor may be heated before, during and after distribution of the silicone composition. In one embodiment, this method may use material for two different purposes, constructing the object and supporting overhangs in order to avoid extruding material into the air. If the object has been printed using supporting equipment or supporting structures once the printing process has ended, it is generally removed (for example by washing with water), leaving the finished object behind.

After printing, the resulting articles may be submitted to various types of post-treatment. In one embodiment, the method further comprises the step consisting of heating the silicone elastomer article obtained by 3D printing. Heating may be used for speeding up the treatment. In another embodiment, the method further comprises the step of additional irradiation of the silicone elastomer article obtained by 3D printing. Additional irradiation may be used for speeding up the treatment. In another embodiment, the method further comprises both steps consisting of heating and irradiating the silicone elastomer article obtained by 3D printing. As an option, steps of post-treatment may greatly improve the surface quality of the printed articles. Grinding is a common means of reducing or removing the layers that are visibly different from the model. Spraying or coating of the surface of the elastomer article with a heat- or UV-hardenable RTV or LSR silicone composition may be used to obtain a smooth and straight surface finish. Laser surface treatment may also be applied. For medical applications, sterilization of the final elastomer article may be obtained by heating the object to a temperature above 100° C.

The invention further relates to the following compounds (1) to (25)

(1)

(2)

(3)

(4)

(5)

(6)

(7)

(8)

(9)

(10)

(11)

-continued (12)

(13)

(14)

(15)

(16)

(17)

(18)

(19)

(20)

(21)

(22)

(23)

(24)

(25)

Neodecanoic acid is a mixture of carboxylic acids with the common structural formula $C_{10}H_{20}O_2$, a molecular weight of 172.26 g/mol and the number CAS=26896-20-8. The components of the mixture are acids having the common property of a "trialkylacetic acid" having three alkyl groups on carbon two, comprising: 2,2,3,5-tetramethylhexanoic acid, 2,4-dimethyl-2-isopropylpentanoic acid, 2,5-dimethyl-2-ethylhexanoic acid and 2,2-dimethyloctanoic acid.

For the following structures (19) to (22), (24) and (25), the neodecanoic acid used for synthesis of the photoinitiators is branched with the various acids stated above.

The invention also relates to the use of compounds (1) to (25) described above as free-radical photoinitiators, and preferably the use of compounds (1) to (25) described above as free-radical photoinitiators for crosslinking silicone compositions.

The following examples are given for purposes of illustration and are not limiting. They notably allow better understanding of the invention and illustration of all its advantages.

EXAMPLES

In the following examples, different photoinitiators, organohydrogenopolysiloxanes and polyorganosiloxanes with acrylate functions were used according to the invention and their structures are indicated in the tables given below.

TABLE 1

Photoinitiators

| Name | Molecular weight (g·mol$^{-1}$) | Structure |
|---|---|---|
| Benzophenone BP from Rahn Comparative | 182 | (benzophenone structure) |
| Isopropyl-thioxanthone ITX Comparative | 254.35 | (isopropyl-thioxanthone structure) |
| Xanthone XT Comparative | 196.19 | (xanthone structure) |
| Thioxanthone TX Comparative | 212.27 | (thioxanthone structure) |
| 2-hydroxy-thioxanthone 2 OH-TX Invention | 228 | (2-hydroxy-thioxanthone structure, OH) |
| 2-hydroxy-anthone 2 OH-TX Invention | 212 | (2-hydroxy-xanthone structure, OH) |
| 2 Hex-XT(1) Invention | 296 | (xanthone with OC$_6$H$_{13}$) |
| 2 Dod-XT (4) Invention | 380 | (xanthone with OC$_{12}$H$_{25}$) |
| 2 neodeca-XT (19) Invention | 366 | (xanthone with O-C(O)-C$_9$H$_{19}$) |
| 2 Hex-TX (5) Invention | 312 | (thioxanthone with OC$_6$H$_{13}$) |
| 2 Dod-TX (8) Invention | 396 | (thioxanthone with OC$_{12}$H$_{25}$) |
| 2 neodeca-TX (20) Invention | 382 | (thioxanthone with O-C(O)-C$_9$H$_{19}$) |

Among these photoinitiators, compounds (1), (4), (5), (8), (19) and (20) were synthesized according to the protocols explained hereunder.

Synthesis of 2-hydroxyxanthone (2 QH-XT)

Reagents:
2-iodobenzoic acid
4-methoxyphenol
cesium carbonate
copper(I) chloride
tris[2-(2-methoxyethoxy)ethyl]amine (TDA-1)
1,4-dioxane
concentrated sulfuric acid Charge a single-necked flask with 1 equivalent of 2-iodobenzoic acid, 1.4 equivalents of 4-methoxyphenol and 2.8 equivalents of cesium carbonate in 6 mL of 1,4-dioxane per mmol of 2-iodobenzoic acid. Stir for 10 min at room temperature, under argon. Then add 0.1 equivalent of copper (I) chloride and 0.1 equivalent of TDA-1. Leave to react for 20 h under reflux under argon.

Once the reaction has ended, evaporate the 1,4-dioxane in a rotary evaporator. Dissolve the residue with 10 wt % solution of Na$_2$CO$_3$ and filter the solution. Then put the filtrate in a separating funnel and wash it with a toluene/ethyl acetate 50/50 mixture. Recover the aqueous phase and acidify before filtering to obtain the reaction intermediate. (Yield: 75%)

Charge a single-necked flask with 1 equivalent of the intermediate in 1.25 mL of concentrated sulfuric acid per mmol of reagent. Leave to react until the spot of the product with a methoxy disappears in TLC (about 3 h). Once the reaction has ended, leave the reaction mixture to cool before pouring it into 10 times the volume of acid in ice. Then extract the solution obtained 3 times with ethyl acetate. The organic phases are collected, dried and evaporated. The product obtained is a white solid. It is possible to recrystallize it in acetone (Yield: 48%). The NMR spectrum corresponds to 2-hydroxyxanthone.

Synthesis of 2-hydroxythioxanthone (2 OH-XT):
Reagents:
thiosalicylic acid
phenol
sulfuric acid Slowly charge a single-necked flask with 1 equivalent of thiosalicylic acid in 1 mL of sulfuric acid per mmol of thiosalicylic acid. Stir vigorously for 10 minutes. Then add 5 equivalents of phenol in the course of 30 minutes. Then leave the mixture to react for 1 h at room temperature, then 2 h at 80° C. and leave to stand overnight at room temperature.

Once the reaction has ended, pour the reaction mixture into 10 times the volume of sulfuric acid in boiling water, and leave to boil for 10 min. Filter the solution once it has cooled. The product obtained is a yellow powder (Yield: 62%). The NMR spectrum corresponds to 2-hydroxythioxanthone.

Figure 1:
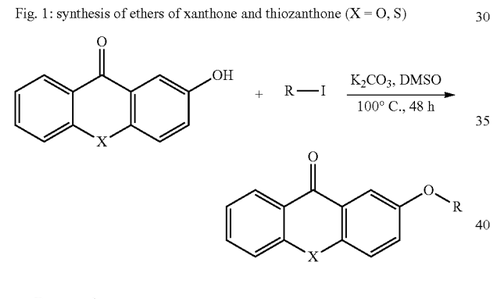

Synthesis of the Ethers of Xanthone and Thioxanthone, Compounds (1), (4), (5), (8)
Reagents:
2-hydroxyxanthone and 2-hydroxythioxanthone
iodoalkane (1-iodohexane and 1-iodododecane)
potassium carbonate
dimethylsulfoxide DMSO
Balanced Equation:

Fig. 1: synthesis of ethers of xanthone and thiozanthone (X = O, S)

Protocol:
Charge a single-necked flask with 1 equivalent of 2-hydroxyxanthone (or of 2-hydroxythioxanthone) and 2 equivalents of potassium carbonate in 5 mL of DMSO per mmol of product. Stir for 10 min at room temperature under argon. Then add the iodoalkane (1-iodohexane or 1-iodododecane) dropwise, and then leave to react at 100° C. under argon for 48 h.

Once the reaction has ended, add 10 times the volume of the reaction mixture to water and extract the mixture 3 times with n-hexane. The organic phases are then collected, dried and evaporated. The crude product obtained is then purified on silica gel with an eluent of 90/10 cyclohexane/ethyl acetate (Yield: about 66%).

Synthesis of the Compounds 2 Neodeca-XT (19) and 2 Neodeca-TX (20)

Charge a single-necked flask with 1 equivalent of 2-hydroxyxanthone (or of 2-hydroxythioxanthone), 1 equivalent of neodecanoic acid and 1 ml of concentrated sulfuric acid per mmol of product. Stir for 2 hours at room temperature under argon. Then leave to react at 120° C. under argon for 12 h.

Once the reaction has ended, add 10 times the volume of the reaction mixture to water and extract the mixture 3 times with n-hexane. The organic phases are then collected, neutralized with sodium carbonate, dried and evaporated. The crude product obtained is then purified on silica gel with an eluent of 90/10 cyclohexane/ethyl acetate.

TABLE 2

| | Organohydrogenopolysiloxane | | |
|---|---|---|---|
| Compound | Name/Supplier | Position of the Si—H units | Content of Si—H (mol/100 g) |
| Hyd 1 | AB 112087 ® Company ABCR Chemical | middle of chain | 1.41 |
| Hyd 2 | BLUESIL ® FLD 626V25H7 Company Bluestar Silicones | end and middle of chain | 0.707 |

The compounds Hyd 1 and Hyd 2 specified in the above table are linear organohydrogenopolysiloxanes with SiH units arranged in the middle and/or end of chain.

Acrylic Silicones
A polyorganosiloxane Acryl 1 of formula with x=85 and n=7 is used in the compositions.

Silicone Compositions Crosslinking by Irradiation:

Tests were carried out to illustrate the use of the type II photoinitiators according to the invention with an organohydrogenopolysiloxane as photoinitiator for polymerizing acrylic silicones. The preparations are carried out as follows: weigh and add 1.2 10-4 mol of the photoinitiator to 2 g of polyorganosiloxane Acryl 1. Stir the whole for 12 hours. Then add 1 wt % of the organohydrogenopolysiloxane Hyd 1.

Two types of crosslinking by irradiation were tested:
  90 seconds of UV radiation with a mercury-xenon lamp. The lamp power is fixed at 510 mW/cm², and
  90 seconds of LED radiation 365 nm with a power of 750 mW/cm² for the xanthone derivatives or under LED radiation 395 nm with a power of 680 mW/cm² for the thioxanthone derivatives.

The manipulations were performed in laminate in order to avoid any effect of inhibition of the reactive species by oxygen. When the manipulations are performed in laminate, the formulation is placed between two sheets of polypropylene, and then between two pellets of $CaF_2$.

The polymerization kinetics is monitored by real-time Fourier transform infrared (RT-FTIR, Vertex 70 from Brucker Optik). This spectroscopy technique consists of exposing the sample simultaneously to light and to infrared radiation in order to monitor the changes in the IR spectrum at 1636 cm$^{-1}$, which is a characteristic band of the C=C bond of the acrylic functions.

The degree of conversion of C=C to C—C during polymerization is directly linked to decrease in calculated area under the peak at 1636 cm$^{-1}$ according to the following equation: conversion (%)=$(A_0-A_t)/A_0 \times 100$, where $A_0$ is the area under the peak before irradiation and $A_t$ is the area under the peak at each timepoint t of irradiation.

For the tests carried out with the mercury-xenon lamp, the plot as a function of time makes it possible to find the final degree of conversion, but also other important parameters, such as the maximum rate of conversion Rp expressed in the following tables as Rp/[M]$_0 \times 100$ where [M]$_0$ is the initial concentration of acrylate function. The maximum rate of conversion Rp is determined from the slope of the curve conversion (%)=f(time) at its inflection point.

The results are presented in Tables 3 and 4 below.

TABLE 3

| Example | Photoinitiator PI | Solubility of PI in compound A1* | Absorption λ max (nm) | LED (365 nm) % conversion of acrylates after 90 s | LED (395 nm) % conversion of acrylates after 90 s |
|---|---|---|---|---|---|
| Comp 2 | Thioxanthone TX | − | 378 | | 16 |
| Ex-1 | 2 OH-TX | − | 400 | | 24 |
| Ex-5 | 2 Hex-TX (5) | + | 400 | | 55 |
| Ex-6 | 2 Dod-TX (8) | ++ | 400 | | 63 |
| Comp 1 | Xanthone XT | − | 340 | 24 | |
| Ex-2 | 2 OH-XT | − | 360 | 71 | |
| Ex-3 | 2 Hex-XT(1) | + | 360 | 75 | |
| Ex-4 | 2 Dod-XT (4) | + | 360 | 89 | |

*−: low solubility <50%; +: partial solubility >50%, ++: soluble
Observations made after stirring for 12 h with a magnetic stirrer The photoinitiators according to the invention give a better degree of conversion after 90 s of irradiation with LEDs.

TABLE 4

Results with Hg—Xe lamp

| Example | Photoinitiator | Absorption λ max (nm) | Rp[M]$_0$ × 100 | Conversion (%) |
|---|---|---|---|---|
| Comp 3 | Xanthone XT | 340 | 1.2 | 55 |
| Ex-7 | 2 OH-XT | 360 | 2.6 | 90 |
| Ex-8 | 2 Hex-XT (1) | 360 | 3.5 | 93 |
| Ex-9 | 2 Dod-XT (4) | 360 | 7.7 | 100 |
| Ex-10 | 2 neodeca-XT (19) | 345 | 4.4 | 100 |

The photoinitiators according to the invention give a better degree of conversion after 90 s of irradiation with an Hg—Xe lamp.

Silicone compositions crosslinking by irradiation and thermally:

The formulations tested are detailed in Table 5 below.

The formulations are prepared by simple mixing of all of the constituents in a high-speed mixer, mixing at 1000 rev/min for one minute.

In addition to the compounds already described above, the following compounds are used:

Oil Vinyl 1: polydimethylsiloxane oil blocked at each chain end with a (CH$_3$)$_2$ViSiO$_{1/2}$ unit, having a viscosity of 60000 mPa·s.

Resin Vinyl 2: polyorganosiloxane of formula MM$^{Vi}$Q containing 1.1 wt % of vinyl groups.

Hydrosilylation catalyst: platinum metal, added in the form of an organometallic complex at 10 wt % of platinum metal, known by the name Karstedt catalyst, Inhibitor: ethynyl-1-cyclohexanol-1 or ECH, Filler: Aerosil @200 from the company Evonik, Polydimethylsiloxane PDMS of viscosity 50 mPa·s

TABLE 5

Silicone compositions crosslinking with free radicals and by polyaddition

| Formulation | A1 parts by weight Comparative | A2 parts by weight Invention | B parts by weight Invention |
|---|---|---|---|
| Acryl 1 | 20 | 20 | 0 |
| Vinyl 2 | 16.1 | 16.1 | 14.7 |
| Vinyl 1 | 27.7 | 27.7 | 25.6 |
| Aerosil ®200 | 1.5 | 1.5 | 1.5 |
| PDMS | 5.54 | 5.54 | 0 |
| Pt | 100 ppm | 100 ppm | 0 |
| Isoprylthioxanthone ITX diluted in xylene | 0.35 ITX 0.70 Xylene | 0 | 0 |
| 2 Dod-XT (4) | 0 | 0.35 | 0 |
| Hyd 2 | 0 | 0 | 8.2 |
| Ethynyl Cyclohexanol | 0 | 0 | 500 ppm |
| Total | 71.9 | 71.2 | 50 |

Two compositions are obtained:

Composition 1 by mixing A1+B, which is a comparative example.

Composition 2 by mixing A2+B, which is an example according to the invention. At 23° C., the dynamic viscosity of composition 2 is equal to 15400 mPa·s.

3D Printing Test 100 g of composition is put in the reservoir of a 3D printer using tank photopolymerization with 365 nm LEDs. It is a DLP Prodway® 3D printer with a twin-cartridge system equipped with a static mixer. The bath life or "potlife" of the composition obtained in the dark (away from the light) is 24 hours before undergoing gelation.

The results for the crosslinking conditions necessary for the first layer with a thickness of 250 μm deposited on a plate and exposed for 5.5 s to UV LED radiation of 365 nm and with an intensity of 75.5 mW/cm² are presented in Table 6 below.

TABLE 6

Energy required for radiation crosslinking of a 250-μm layer of the silicone compositions

| Optical properties | Composition 1 Comparative | Composition 2 Invention |
|---|---|---|
| Ec(mJ/cm²) | 270 | 110 |
| $E_4$ (mJ/cm²) (100 μm) | 355 | 140 |
| $E_8$ (mJ/cm²) (200 μm) | 416 | 178 |
| $E_{10}$ (mJ/cm²) (250 μm) | 515 | 225 |

In the following table, Ec represents the critical surface energy measured in mJ/cm².

The composition according to the invention has a lower critical surface energy. Less energy will have to be supplied to it to reach the gel point. This composition therefore offers the advantage of requiring less energy for crosslinking and consequently it will be possible to print the successive layers more quickly.

E4 is the energy to be supplied to achieve crosslinking on a thickness of 100 microns, E8 to achieve 200 microns and E10 to achieve 250 microns.

TABLE 7

Mechanical properties measured according to standard NF EN ISO 527 on the silicone elastomers obtained after crosslinking by irradiation and thermally

| Mechanical properties | Composition 1 Comparative | Composition 2 Invention |
|---|---|---|
| Breaking strength (MPa) | 1.65 | 1.65 |
| Elongation at break (%) | 65 | 65 |
| Tension modulus (MPa) | 2.54 | 2.54 |

The invention claimed is:

1. A silicone composition C1 crosslinkable by exposure to radiation with a wavelength between 300 and 450 nm, comprising:
    at least one polyorganosiloxane A comprising at least one (meth)acrylate group bound to a silicon atom,
    at least one organohydrogenopolysiloxane H comprising at least two, and optionally at least three hydrogen atoms each bound to different silicon atoms, and
    at least one free-radical photoinitiator P of the following formula (I):

in which:
   the symbol X is selected from the group consisting of: an oxygen atom, a sulfur atom, and a CH₂ group,
   the symbols $R^2$ and $R^4$ are hydrogen atoms,
   the symbols $R^1$ and $R^3$, which may be identical or different, are selected from the group consisting of: a hydrogen atom, a hydroxyl and a group of formula —OZ with the symbol O being an oxygen atom and the symbol Z being selected from the group consisting of:
     a $C_1$-$C_{20}$, optionally $C_3$-$C_{20}$, alkyl group or $C_2$-$C_{20}$ alkenyl group,
     a group —(C=O)—$R^5$, with the radical $R^5$ being selected from the $C_1$-$C_{20}$ alkyl, $C_2$-$C_{20}$ alkenyl, $C_3$-$C_{20}$ cycloalkyl and $C_6$-$C_{12}$ aryl groups, and
     a group —Si($R^6$)₃, where the groups $R^6$, which may be identical or different, are selected from the $C_1$-$C_{20}$ alkyl, $C_2$-$C_{20}$ alkenyl, $C_3$-$C_{20}$ cycloalkyl, $C_6$-$C_{12}$ aryl, $C_1$-$C_{20}$ alkoxyl groups and the hydrogen atom,
   and with the condition that at least one of the substituents $R^1$ or $R^3$ is a group of formula —OZ.

2. The composition C1 as claimed in claim 1, in which the photoinitiator P is selected from the compounds of formula (I), in which the symbol X is an oxygen atom or a sulfur atom.

3. The composition C1 as claimed in claim 1, in which the polyorganosiloxane A comprises:
    a1) at least one unit of the following formula (A1):

in which:
   the symbols R, which may be identical or different, each represent a linear or branched $C_1$ to $C_{18}$ alkyl group, a $C_6$ to $C_{12}$ aryl or aralkyl group, optionally substituted, optionally with halogen atoms, or a radical alkoxy-O$R^4$ with $R^4$ being a hydrogen atom or a hydrocarbon radical comprising from 1 to 10 carbon atoms,
   the symbols Z are monovalent radicals of formula -y-(Y')ₙ in which:
   y represents a linear or branched polyvalent $C_1$-$C_{18}$ alkylene radical optionally extended by divalent $C_1$ to $C_4$ oxyalkylene or polyoxyalkylene radicals optionally substituted with a hydroxy radical,
   Y' represents a monovalent alkenylcarbonyloxy radical, and
   n is equal to 1, 2 or 3, and
   "a" is an integer equal to 0, 1 or 2, b is an integer equal to 1 or 2 and the sum a+b=1, 2 or 3; and
   a2) optionally units of the following formula (A2):

in which:
the symbols R, which may be identical or different, each represent a linear or branched $C_1$ to $C_{18}$ alkyl group, a $C_6$ to $C_{12}$ aryl or aralkyl group, optionally substituted, optionally with halogen atoms, and
"a" is an integer equal to 0, 1, 2 or 3.

4. The composition C1 as claimed in claim 1, in which the concentration of free-radical photoinitiator P is between 0.0003 and 0.015 mol per 100 g of composition C1.

5. A method for preparing silicone film with release properties, comprising crosslinking a composition C1 as claimed in claim 1 by exposure to radiation with a wavelength between 300 nm and 450 nm.

6. The method as claimed in claim 5, in which the radiation is generated by light-emitting diodes.

7. A silicone composition C2 crosslinkable thermally and by exposure to radiation with a wavelength between 300 and 450 nm comprising:
at least one composition C1 as claimed in claim 1,
at least one polyorganosiloxane B comprising at least two alkenyl groups each bound to a silicon atom, and
at least one hydrosilylation catalyst.

8. The silicone composition C2 as claimed in claim 7, further comprising at least one additive selected from the group consisting of:
an inhibitor I,
a filler F, and
an adhesion promoter G.

9. A silicone elastomer obtained by crosslinking a composition C1 as claimed in claim 1.

10. A product comprising the composition C2 as claimed in claim 7, for preparing one or more articles made of silicone elastomer by an additive manufacturing process.

11. A method for preparing one or more articles made of silicone elastomer, comprising crosslinking a composition C2 as claimed in claim 7 by exposure to radiation with a wavelength between 300 nm and 450 nm.

12. The method as claimed in claim 11, in which the radiation is generated by light-emitting diodes.

13. The method as claimed in claim 11 further comprising heating.

14. The composition C1 as claimed in claim 1, wherein the at least one free-radical photoinitiator P is a compound selected from the following formulas (1) to (4), (6) to (8), (13) to (16), (19) to (22), and (24) to (25):

(1)

(2)

(3)

-continued

(4)

(6)

(7)

(8)

(13)

(14)

(15)

(16)

(19)

(20)

(22)

(24)

(25)

* * * * *